(12) United States Patent
Hoover et al.

(10) Patent No.: US 9,475,633 B2
(45) Date of Patent: Oct. 25, 2016

(54) PORTABLE CASSETTE FOR DISPENSING MEDICATION AND METHOD THEREOF

(71) Applicant: Xerox Corporation, Norwalk, CT (US)

(72) Inventors: Linn C. Hoover, Webster, NY (US);
Paul R. Austin, Webster, NY (US);
Steven R. Moore, Pittsford, NY (US)

(73) Assignee: Xerox Corporation, Norwalk, CT (US)

( * ) Notice: Subject to any disclaimer, the term of this patent is extended or adjusted under 35 U.S.C. 154(b) by 267 days.

(21) Appl. No.: 14/183,904

(22) Filed: Feb. 19, 2014

(65) Prior Publication Data

US 2015/0232256 A1 Aug. 20, 2015

(51) Int. Cl.
*A61J 7/04* (2006.01)
*B65D 83/04* (2006.01)
*G06F 19/00* (2011.01)
*A61J 7/00* (2006.01)

(52) U.S. Cl.
CPC .......... *B65D 83/0454* (2013.01); *A61J 7/0069* (2013.01); *A61J 7/0084* (2013.01); *A61J 7/0418* (2015.05); *G06F 19/3456* (2013.01); *G06F 19/3462* (2013.01); *A61J 2200/30* (2013.01)

(58) Field of Classification Search
CPC .... A61J 7/0481; A61J 7/0069; A61J 7/0084; A61J 7/0418; G06F 19/3456; G06F 19/3462; B65D 83/0454
USPC ................... 221/122; 700/236, 242
See application file for complete search history.

(56) References Cited

U.S. PATENT DOCUMENTS

| | | | |
|---|---|---|---|
| 4,572,403 A * | 2/1986 | Benaroya ................. | A61J 7/04 700/243 |
| 4,616,316 A | 10/1986 | Hanpeter | |
| 4,748,600 A * | 5/1988 | Urquhart ............... | A61J 7/0409 221/15 |
| 6,145,697 A * | 11/2000 | Gudish ................. | A61J 7/0409 221/7 |
| 6,163,736 A * | 12/2000 | Halfacre ............... | A61J 7/0481 221/102 |
| 6,471,087 B1 * | 10/2002 | Shusterman ......... | A61J 7/0084 221/2 |
| 6,705,487 B2 * | 3/2004 | Kim .................... | G07F 17/0092 221/281 |
| 7,336,564 B2 | 2/2008 | Feodoroff | |
| 7,454,880 B1 | 11/2008 | Austin | |

(Continued)

OTHER PUBLICATIONS

Database Systems Corp., "Care Call Reassurance", http://www.call-reassurance.com/, (2012).

(Continued)

*Primary Examiner* — Timothy Waggoner
(74) *Attorney, Agent, or Firm* — Simpson & Simpson, PLLC

(57) ABSTRACT

An apparatus for dispensing medications, including: a portable cassette including with a body portion including a plurality of cassette compartments and at least one lid displaceable with respect to the body portion to enable access to the cassette compartments in a predetermined sequence; and a pill-dispenser including at least one dispensing compartment arranged to store respective pills of at least one respective medication; a dispensing element configured to release the respective pills from the at least one dispensing compartment; and a cassette element arranged to receive the portable cassette and displace the portable cassette so that at least one of the in respective pills falls into each cassette compartment. After the at least one of the respective pills fall into said each cassette compartment: the portable cassette is removable from the pill-dispenser; and the lid is displaceable to control access to the cassette compartments.

32 Claims, 9 Drawing Sheets

(56) References Cited

U.S. PATENT DOCUMENTS

| | | | | |
|---|---|---|---|---|
| 7,922,037 | B2* | 4/2011 | Ohmura | A61J 7/0084 221/123 |
| 8,068,934 | B2* | 11/2011 | Saltsov | A61J 7/0084 700/242 |
| 2003/0057231 | A1* | 3/2003 | Kim | G07F 17/0092 221/263 |
| 2003/0127463 | A1* | 7/2003 | Varis | A61J 7/0084 221/2 |
| 2012/0024889 | A1* | 2/2012 | Robertson | A61B 5/0002 222/192 |

OTHER PUBLICATIONS e-pill, LLC, "e-pill Medication Reminders", http://www.epill.com/, (2012).

MediMemory, Personal Medication Monitoring Management, http://medimemory.com/, (2012).

* cited by examiner

PORTABLE CASSETTE FOR DISPENSING MEDICATION AND METHOD THEREOF

TECHNICAL FIELD

The present disclosure relates to a portable cassette including a plurality of compartments in which are stored a plurality of medications and a sensor, memory element; and processor configured to sense and store data regarding access to compartments. The present disclosure relates to an apparatus for dispensing medications including a portable cassette for storing medications and a pill-dispenser arranged to dispense medications into compartments for the cassette. The pill-dispenser is configured to evaluate medication compliance after the cassette has been filled, removed, and re-inserted by identifying medications remaining in the compartments.

BACKGROUND

Medication adherence, including patient adherence to medication regimens is an important aspect of any system providing medical services. Specifically, lack of medical adherence has a negative effect on outcomes and increases costs associated with providing medical services. For example, research shows that:

1. Approximately 25% of patients prescribed medications for a new illness fail to fill their initial prescription;
2. Approximately half of patients taking maintenance medications for a chronic disease stop taking their medications within the first year; and,
3. The estimated cost of unnecessary medical treatment attributable to medication non-adherence is $290 B annually.

It is known to use home-based medication dispensers. For example, the patient or a designated caregiver is required to periodically pre-load the appropriate pills into provided cups, according to each pill's dosage regimen. The pre-loaded cups are then placed into the dispenser. The dispenser then releases each cup's contents at a designated time. However, home-based medication dispensers do not accommodate time periods during which a patient is away from the dispenser and medication dosages are needed. The dispenser may be able to dispense the medications en masse for the time period; however, the user is forced to sort the pills as needed for various dosages at various times. Further, the home-based medication dispensers have no means of determining compliance with a medication regimen during the time period.

SUMMARY

According to aspects illustrated herein, there is provided a portable cassette for dispensing medications, including: a body portion including a plurality of compartments arranged to receive respective pills of respective medications; at least one lid displaceable with respect to the body portion to enable access to the plurality of compartments in a predetermined sequence; a sensor configured to detect when the at least one lid is displaced to enable access to the plurality of compartments; a memory element; and a first processor configured to store, in the memory element, respective times for each detection, by the sensor, of displacement of the at least one lid.

According to aspects illustrated herein, there is provided an apparatus for dispensing medications, including: a portable cassette including with a body portion including a plurality of cassette compartments and at least one lid displaceable with respect to the body portion to enable access to the plurality of cassette compartments in a predetermined sequence; and a pill-dispenser including at least one dispensing compartment arranged to store respective pills of at least one respective medication; a dispensing element configured to release the respective pills from the at least one dispensing compartment; and a cassette element arranged to receive the portable cassette and displace the portable cassette so that at least one of the respective pills falls into each cassette compartment included in the plurality of cassette compartments. After the at least one of the respective pills fall into said each cassette compartment: the portable cassette is removable from the pill-dispenser; and the at least one lid is displaceable to control access to the plurality of cassette compartments.

According to aspects illustrated herein, there is provided an apparatus fir dispensing medications, including: a portable cassette with a body portion including a plurality of cassette compartments and at least one lid displaceable with respect to the body portion to enable access to the plurality of cassette compartments in a predetermined sequence; and a pill-dispenser including at least one dispensing compartment arranged to store respective pills of at least one respective medication; a dispensing element; a cassette element arranged to receive the portable cassette; a memory element; and a processor configured to: receive prescription information including at least one dosage for the at least one medication and at least one schedule for taking the at least one medication; operate the dispensing element, according to the prescription information, to release the respective pills from the at least one dispensing compartment; operate the cassette element, according to the prescription information, to displace the portable cassette so that at least one of the respective pills falls into each cassette compartment included in the plurality of cassette compartments; determine when the portable cassette has been removed from and reinserted in the cassette element; operate the cassette element to identify cassette compartments containing a respective pill; transmit the identification of the cassette compartments to a computer associated with a health care provider or an entity providing the at least one medication, or store the identification of the cassette compartments in the memory element; receive, from the computer, the prescription information modified according to the identification of the cassette compartments, or modify the prescription information according to the identification of the cassette compartments; and control the dispensing element and displace the portable cassette according to the modified prescription information.

According to aspects illustrated herein, there is provided a method of dispensing medications, comprising: receiving, in a pill-dispenser, a portable cassette; releasing, from at least one dispensing compartment for the pill-dispenser, at least one pill of at least one respective medication stored in the at least one dispensing compartment; displacing the portable cassette within the pill-dispenser; receiving at least one of the respective pills into each cassette compartment included in a plurality of cassette compartments of the portable cassette; and after the portable cassette is removed from the pill-dispenser, limiting displacement of at least one lid for the portable cassette to control access to the plurality of cassette compartments.

According to aspects illustrated herein, there is provided a method of dispensing medications, including: placing, in each compartment included in a plurality of compartments of a body portion of a portable cassette, at least one respective pill of at least one respective medication; detecting, with a sensor, when at least one lid of the portable cassette is displaced to enable access to the plurality of compartments; and storing, using a first processor and in a memory element, respective times for each detection, by the sensor, of displacement of the at least one lid.

According to aspects illustrated herein, there is provided a method of dispensing medications, including: receiving, using a processor for a pill-dispenser, prescription information including at least one dosage for at least one medication and at least one schedule for taking the at least one medication; receiving, in a pill-dispenser, a portable cassette; releasing, from at least one dispensing compartment for the pill-dispenser, at least one pill of at least one respective medication stored in the at least one dispensing compartment; displacing the portable cassette within the pill-dispenser; receiving at least one of the respective pills into each cassette compartment included in a plurality of cassette compartments of the portable cassette; determining, using the processor, when the portable cassette has been removed from and reinserted in the cassette element; operating, using the processor, the cassette element to identify cassette compartments containing a respective pill; transmitting, using the processor, the identification of the cassette compartments to a computer associated with a health care provider or an entity providing the at least one medication, or storing, using the processor, the identification of the cassette compartments in a memory element for the pill-dispenser; receiving, using the processor and from the computer, the prescription information modified according to the identification of the cassette compartments, or modifying, using the processor, the prescription information; and releasing the at least one pill, displacing the portable cassette, and receiving the at least one of the respective pills in compliance with the modified prescription information.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Moreover, although any methods, devices or materials similar or equivalent to those described herein can be used in the practice or testing of these embodiments, some embodiments of methods, devices, and materials are now described.

Figure 1:
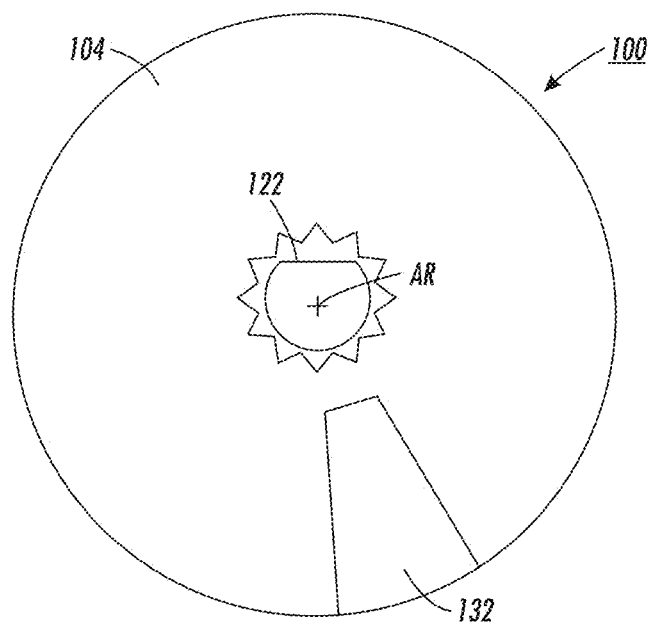
FIG. 1 is a top view of a portable cassette for administering medications.

FIG. 1 is a top view of portable cassette 100 for administering medications.

Figure 2:
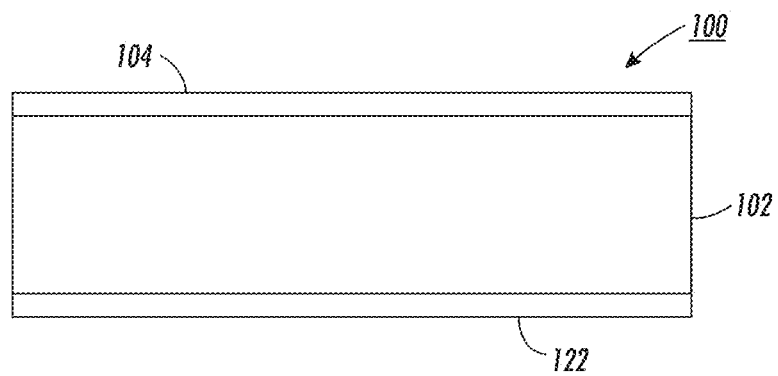
FIG. 2 is a side view of the portable cassette shown in FIG. 1.

FIG. 2 is a side view of portable cassette 100 shown in FIG. 1.

Figure 3:
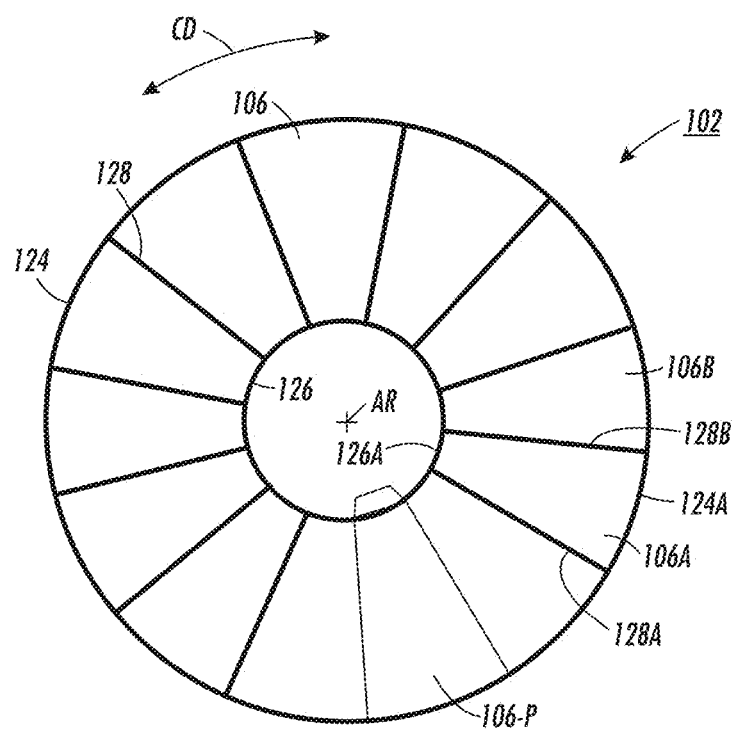
FIG. 3 is a top view of the body portion shown in FIG. 1.

FIG. 3 is a top view of a body portion shown in FIG. 1.

Figure 4:
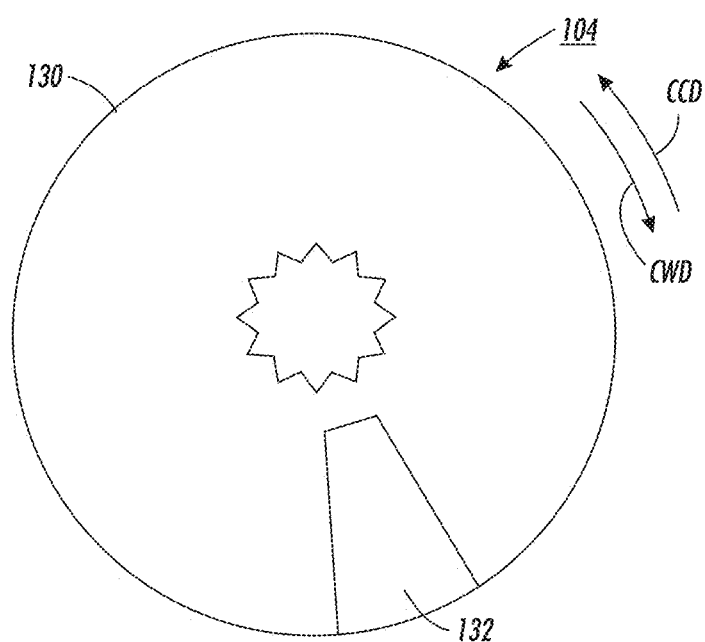
FIG. 4 is a top view of the lid shown in FIG. 1.

FIG. 4 is a top view of the lid shown in FIG. 1.

The following should be viewed in light of FIGS. 1 through 5. Portable cassette 100 includes body portion 102 and at least one lid 104. Body portion 102 includes compartments 106 arranged to receive respective pills P of respective medications. In an example embodiment, at least one lid 104 includes a single lid 104. The discussion that follows is directed to a single lid 104. Lid 104 is displaceable with respect to body portion 102 to enable access to compartments 106 in a predetermined sequence, as further described below. Although a particular number and shape of compartments 106 are shown in FIG. 3, it should be understood that other numbers and shapes of compartments 106 are possible.

Figure 5:
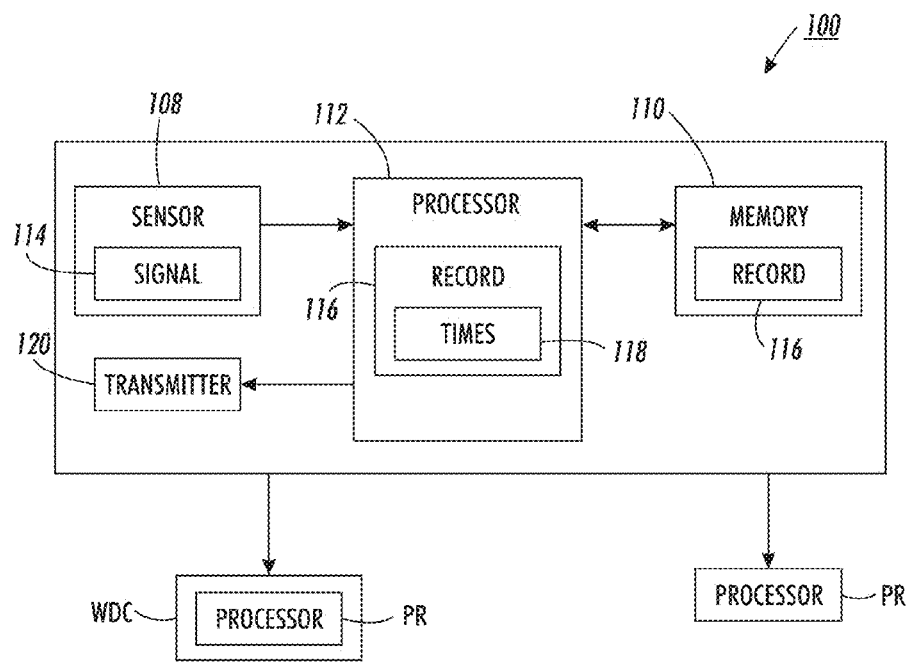
FIG. 5 is a schematic block diagram of portable cassette 100

FIG. 5 is a schematic block diagram of portable cassette 100. In an example embodiment, portable cassette 100 includes sensor 108, memory element 110, and processor 112. Sensor 108 is configured to detect when lid 104 is displaced to enable access to compartments 106 and generate signal 114 for each displacement of lid 104. Processor 112 is configured to receive signals 114 and store a record 116 of signals 114 in memory 110. In an example embodiment, processor 112 is configured to include a respective time 118, for example a respective stamp, in record 116 for each signal 114 received by processor 112. Sensor 108 can be any sensor known in the art, including, but not limited to an accelerometer. Memory element 110 and processor 112 can be any memory element and processor, respectively, known in the art.

Lid 104 is displaceable to enable access to compartments 106 in a predetermined sequence and block access to compartments 106 in a sequence different from the predetermined sequence, as further described below.

In an example embodiment, processor 112 is configured to transmit times 118 to processor PR located outside of portable cassette 100, that is processor PR is not a part of cassette 100. In an example embodiment, processor 112 is configured to transmit times 118 via a hardwire connection. In an example embodiment, cassette 100 includes transmitter 120 and processor 112 is configured to wirelessly transmit times 118 via transmitter 120. For example, processor PR can be part of wireless communications device WCD associated with a patient taking pills P or associated with other persons or entities involved in the health care of a patient taking pills P.

Figure 6:
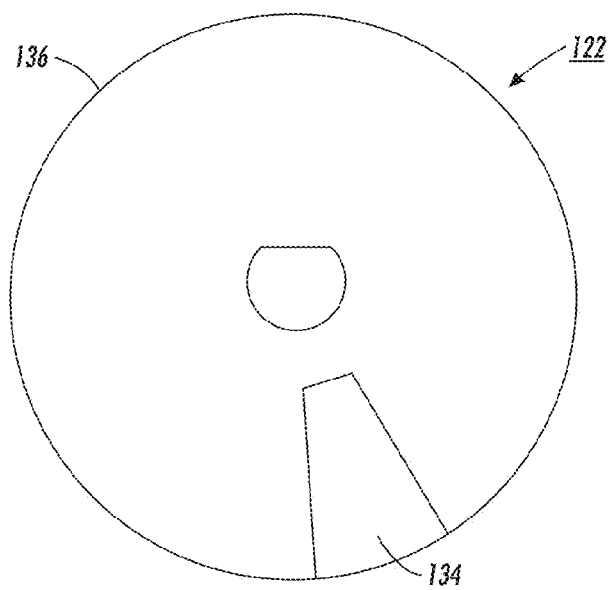
FIG. 6 is a top view of the bottom plate shown in FIG. 1.

FIG. 6 is a top view of the bottom plate shown in FIG. 1. In an example embodiment, cassette 100 includes bottom plate 122 displaceable with respect to portion 102, in an example embodiment, cassette 100 has the substantially cylindrical configuration shown in FIGS. 1 through 4; however it should be understood that cassette 100 is not limited to the configuration shown in FIGS. 1 through 4 and 6. For example, cassette 100 can have other configurations including, but not limited to, a single row of compartments or other geometric shapes with multiple rows and columns of compartments. The discussion that follows is directed to the cylindrical configuration of cassette 100 shown in FIGS. 1 through 4 and 6.

In an example embodiment, portable cassette 100 includes axis of rotation AR. Lid 104 and bottom plate 122 are substantially orthogonal to axis AR. Body portion 102 includes cylindrical outer wall 124 and inner wall 126 centered about axis AR and engaged with lid 104 and bottom plate 122. Wall 126 is radially inward of wall 124. Portion 102 includes dividing walls 128 connecting walls 124 and 126 and tapering toward axis AR. Each compartment 106 is formed by respective portions of inner and outer walls 124 and 126 and a pair of walls 128 adjacent to each other in circumferential direction CD. For example, compartment 106A is formed by segments 124A and 126A of walls 124 and 126, respectively, and side walls 128A and 12813. Thus, in the example of FIGS. 1-4 and 6, compartments 106 are wedge shaped.

Each compartment 106 has shape in plane PL orthogonal to axis AR, for example, the shape shown in FIG. 3. Lid 104 is disc-shaped with radially outer circumference 130 substantially aligned with outer wall 124 in axial direction AD parallel to axis AR. Lid 104 includes opening 132 having a shape substantially matching at least a portion of the shape of compartments 106. Lid 104 is rotatable, about axis AR, with respect to body 102 portion to align opening 132 with a compartment 106 in direction AD, for example, to enable pills P to be removed from the compartment. In an example embodiment, sensor 108 is configured to detect each rotation of lid 104 aligning opening 132 with a respective compartment 106 and processor 112 is configured to store, in memory element 110, respective times 118 for each alignment of opening 132 with the respective compartment 106.

As noted above, lid 104 is configured enable only a predetermined displacement of lid 104. For example, the displacement is controllable such that compartments 106 are accessible in an order compliant with a prescription for pills P and are not accessible in an order out of compliance with the prescription. In an example embodiment, lid 104 is rotatable about axis AR in one of a clockwise direction CWD or counter-clockwise direction CCD and lid 104 is locked against rotation about axis AR in the other of direction CWD or CCD. For example, rotation is enabled in direction CWD and compartments 106 are sequenced according to the days of the week in direction CWD.

In an example embodiment, compartments 106 includes pass-through compartment 106-P. Bottom plate 122 is disc-shaped and includes opening 134 and radially outer circumference 136 substantially aligned with outer wall 124 in direction AD. As further described below, lid 104 and wall 122 can be rotated so that opening 132 and 134 align with compartment 106-P in direction AD to form a passageway through cassette 100.

Figure 7:
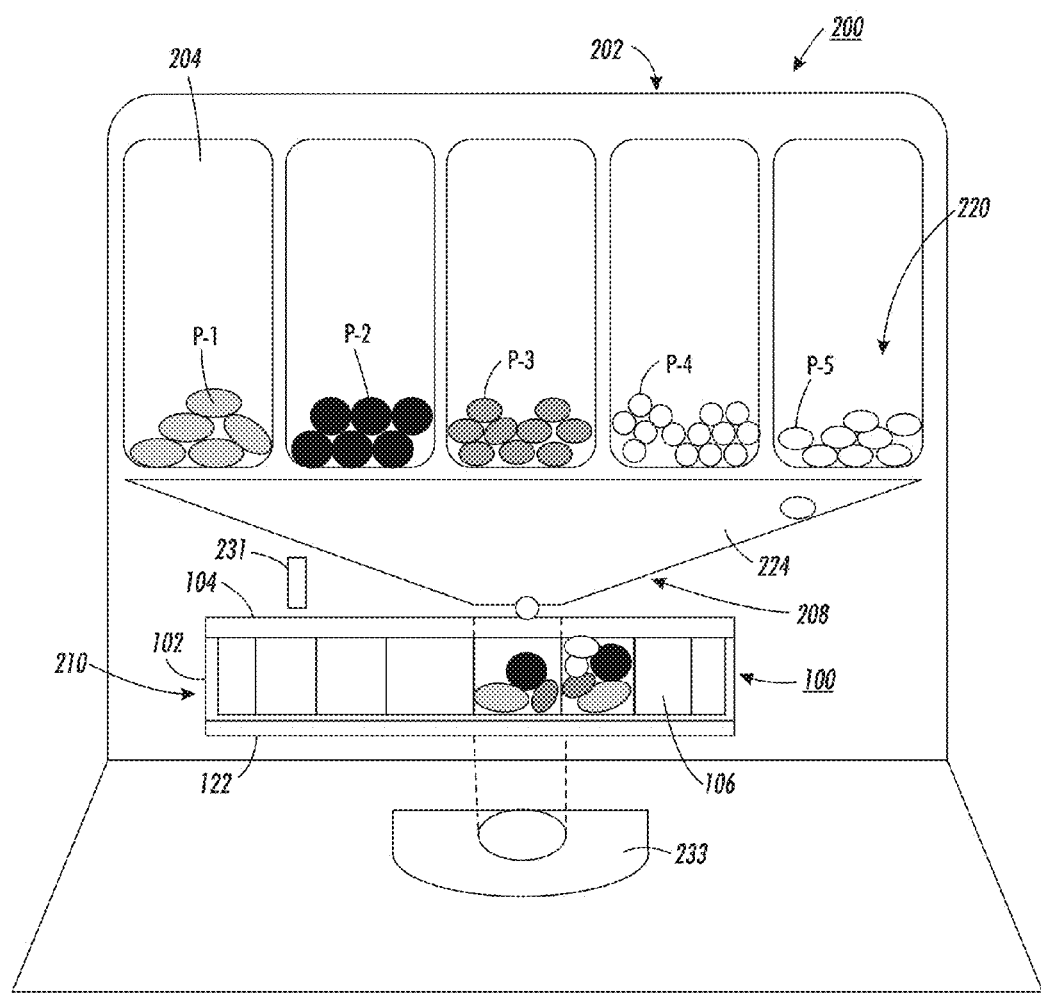
FIG. 7 is a pictorial representation of an apparatus, including the portable cassette shown in FIG. 1, for administering medications, shown dispensing pills into the portable cassette.

FIG. 7 is a pictorial representation of apparatus 200, including portable cassette 100, for administering medications, shown dispensing pills into portable cassette 100. The discussion of cassette 100 in FIGS. 1 through 6 is applicable to cassette 100 and apparatus 200 except as noted. In an example embodiment, cassette 100 does not include sensor 108, memory 110, processor 112, and transmitter 120. Apparatus 200 includes pill-dispenser 202. Dispenser 202 includes at least one dispensing compartment 204 arranged to store respective pills P of at least one respective medication. In the example of FIG. 7 a plurality of compartments 204 are shown and the discussion that follows is addressed to the case including a plurality of compartments 204 each storing a different medication. Each compartment 204 stores different pills, for example, pills P-1, P-2, P-3, P-4, and P-5, for different medications. Dispenser 202 includes dispensing element 208, configured to release respective pills P from compartments 204 and cassette element 210 arranged to receive cassette 100 and displace body portion 102 so that respective pills P fall into respective cassette compartments 106.

Figure 8:
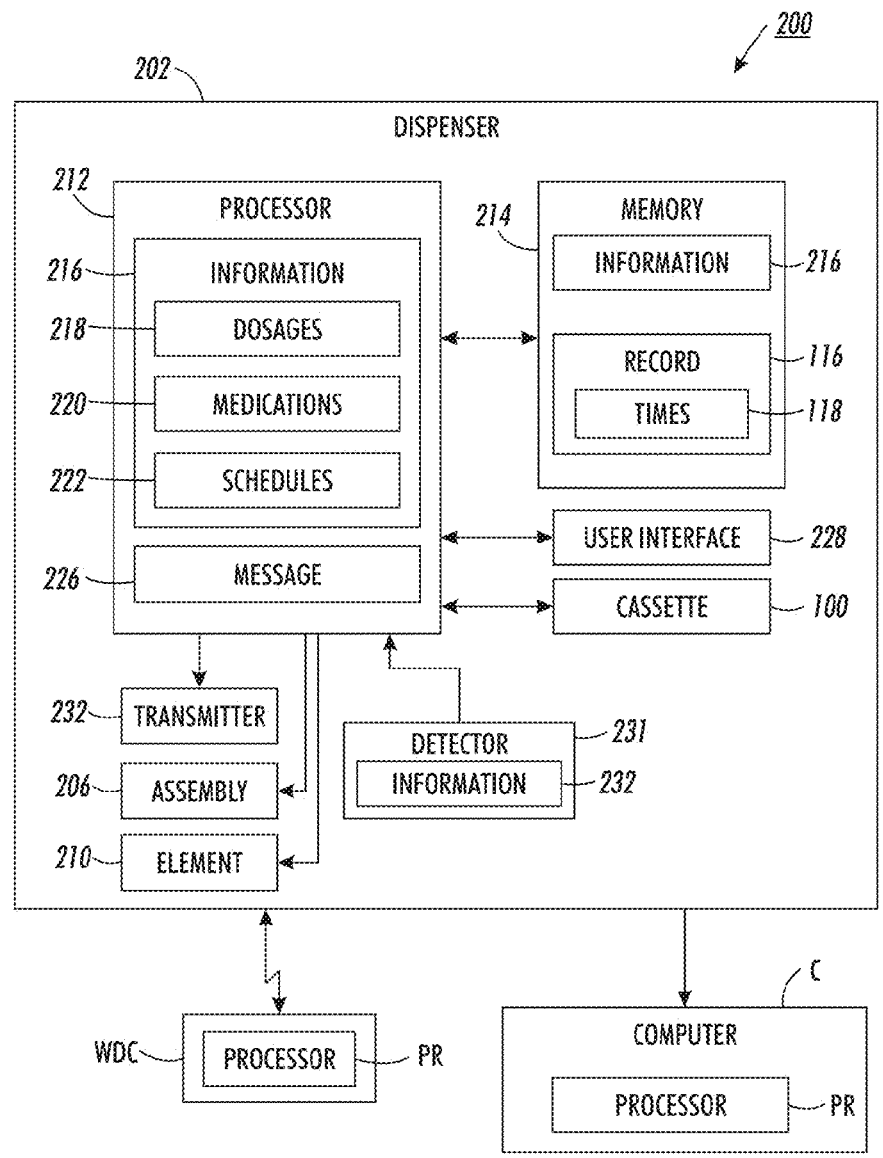
FIG. 8 is a schematic block diagram of the apparatus of FIG. 7.

FIG. 8 is a schematic block diagram of apparatus 200. Dispenser 202 includes processor 212 and memory 214. Processor 212 configured to receive prescription information 216 including a respective dosage 218 for each medication 220 stored in compartments 204 and a respective schedule 222 for taking medications 220. Processor 212 is configured to store information 216 in memory 214, control dispensing element 208 and displace (rotate in the example of FIG. 7) body portion 102 so that respective pills P falling into each cassette compartment 106 are in compliance with the prescription information. That is, the correct type and number of pills P according to information 216 are placed into compartments 106. In an example embodiment, dispensing element 208 includes chute 224 arranged to receive respective pills P and cassette element 210 is configured to displace (rotate) body portion 102 to sequentially align compartments 106 with chute 224 so that the respective pills P fall into compartments 106 in accordance with information 216.

For example, when cassette 100 is inserted into element 210, element 210 rotates lid 104 as necessary so that opening 132 aligns with chute 224. Element 210 then rotates body portion 102 so that compartment 106A in FIG. 3 is aligned with opening 132. Processor 212 associates compartment 106A with Monday and determines medication(s) 220 required for Monday according to information 216. Processor 212 operates element 208 to dispense pills P required for Monday. Element 210 then rotates body portion 102 so that compartment 1069 in FIG. 3 is aligned with opening 132 and chute 224. Processor 212 associates compartment 1069 with Tuesday and determines medication(s) 220 required for Tuesday according to information 216. Processor 212 operates element 208 to dispense pills P required for Tuesday. The process is continued until all compartments 106 are filled or until sufficient compartments 106 are filled to satisfy information 216. If all compartments 106 for a particular cassette 100 are filled before the requirements of information 216 are met, processor 212 sends message 226, for example, on user interface 228, with instructions to insert one or more additional cassettes 100. Element 210 numbers each cassette in a series of multiple cassettes in the order in which the cassettes are to be accessed.

In an example embodiment, processor 112 is configured to transmit record 116 and times 118 to processor 212. Times 118 provide information regarding compliance with information 216, for example, times 118 show if and when compartments 106 have been accessed. Processor 212 can display times 118 on interface 228. In an example embodiment, processor 212 stores times 118 in memory 214. In an example embodiment, processor 212 is configured to transmit times 118 to processor PR for computer C located outside of dispenser 202. That is, computer C is not a part of dispenser 202. Any means known in the art, such as hard wire or wireless transmission can be used to transmit times 118. Computer C can be associated with a health care provider for the patient taking medications 220, an entity prescribing or providing medications 220, or an entity, such as an insurance company, paying for some or all of medications 220. In an example embodiment, dispenser 202 includes transmitter 232 and processor 212 is configured to wirelessly transmit times 118 via transmitter 232. For example, processor PR can be part of wireless communications device WCD associated with a patient taking pills P or associated with other persons or entities involved in the health care of a patient taking pills P.

In an example embodiment, processor 212 is configured to received modified prescription information 216 from computer C and to control dispensing element 208 and cassette element 210, for example to displace cassette 100, according to modified prescription information 216. For example, times 118 indicate when and if compartments 106 have been accessed, indicating compliance with prescription information 216. If times 118 indicate a lack of compliance with prescription information 216, prescription information 216 can be modified by the entity associated with computer C to compensate for the lack of compliance in future dispensing of pills from dispenser 202.

In an example embodiment, processor 212 is configured to modify prescription information 216 according to times 118 and to control dispensing element 208 and cassette element 210, for example to displace the portable cassette, according to modified prescription information 216. For example, times 118 indicate when and if compartments 106 have been accessed, indicating compliance with prescription information 216. If times 118 indicate a lack of compliance with prescription information 216, prescription information 216 can be modified to compensate for the lack of compliance in future dispensing of pills from dispenser 202.

In an example embodiment, cassette 100 does not include sensor 108, memory 110, processor 112, and transmitter 120. Processor 212 is configured to determine when portable cassette 100 has been removed from and reinserted in cassette element 210 and operate cassette element 210 to identify cassette compartments 106 containing a respective pill. Depending on schedule 224 and the duration between removing and reinstalling cassette 100, the presence of a pill or pills in one or more compartments 106 indicates a lack of compliance with prescription information 216; for example, one or more dosages of medications have been missed. In an example embodiment, dispenser 202 includes detection element 231 and cassette element 210 rotates cassette 100 past element 231 so that element 231 detects a presence of a respective pill or pills in compartments 106. Element 231 can be any detection device, for example, an optical detection device, known in the art.

Element 231 is configured to transmit data, including identification 232 of compartments containing a pill or pills, to processor 212. In an example embodiment, processor 212 is configured to transmit identification 232 to computer C and receive modified prescription information 216 from computer C. Processor 212 is configured to control dispensing element 208 and cassette element 210, for example to displace the portable cassette, according to modified prescription information 216. For example, identification 232 indicates if and when compartments 106 have been accessed, indicating compliance with prescription information 216. If identification 232 indicates a lack of compliance with prescription information 216, prescription information 216 can be modified by the entity associated with computer C to compensate for the lack of compliance in future dispensing of pills from dispenser 202.

In an example embodiment, processor 212 is configured to modify prescription information 216 according to identification 232 and to control dispensing element 208 and cassette element 210, for example to displace the portable cassette, according to modified prescription information 216. For example, identification 232 indicates if and when compartments 106 have been accessed, indicating compliance with prescription information 216. If identification 232 indicates a lack of compliance with prescription information 216, prescription information 216 can be modified to compensate for the lack of compliance in future dispensing of pills from dispenser 202.

Figure 9:
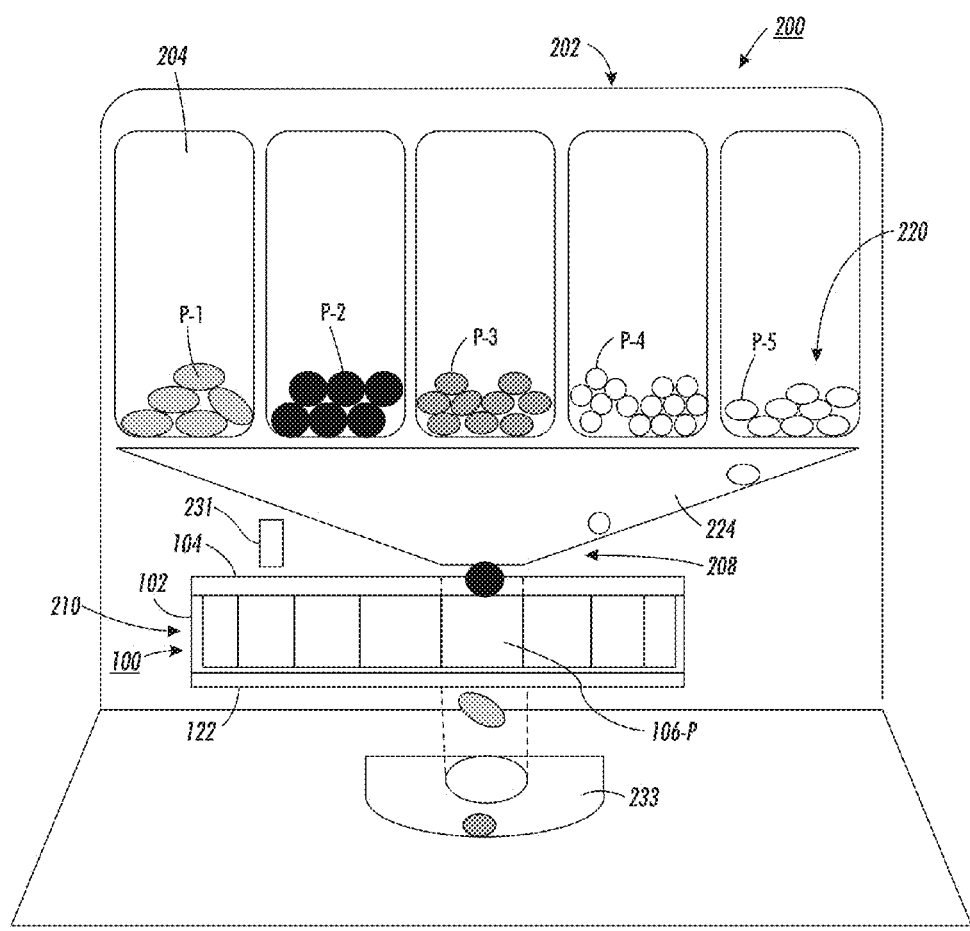
FIG. 9 is a pictorial representation of the apparatus of FIG. 7, dispensing pills through the portable cassette into a tray.

FIG. 9 is a pictorial representation of the apparatus of FIG. 7, dispensing pills through the portable cassette into a tray. As noted in the discussion of cassette 100 in FIGS. 1 through 6, provision is made to enable normal operation of dispenser 202 when cassette 100 is in place, for example, being stored in dispenser 202. By "normal operation" we mean operating dispenser 202 to provide pills P available at dispenser 202, rather than through cassette 100. In an example embodiment, dispenser 202 includes tray 233. For normal operation, element 210 rotates body portion 102, lid 104, and bottom plate 122 so that pass-through compartment 106-P and openings 132 and 134 are aligned with chute 224. Then, dispensing element 208 is able to dispense pills P through cassette 100 as needed into tray 233.

Figure 10:
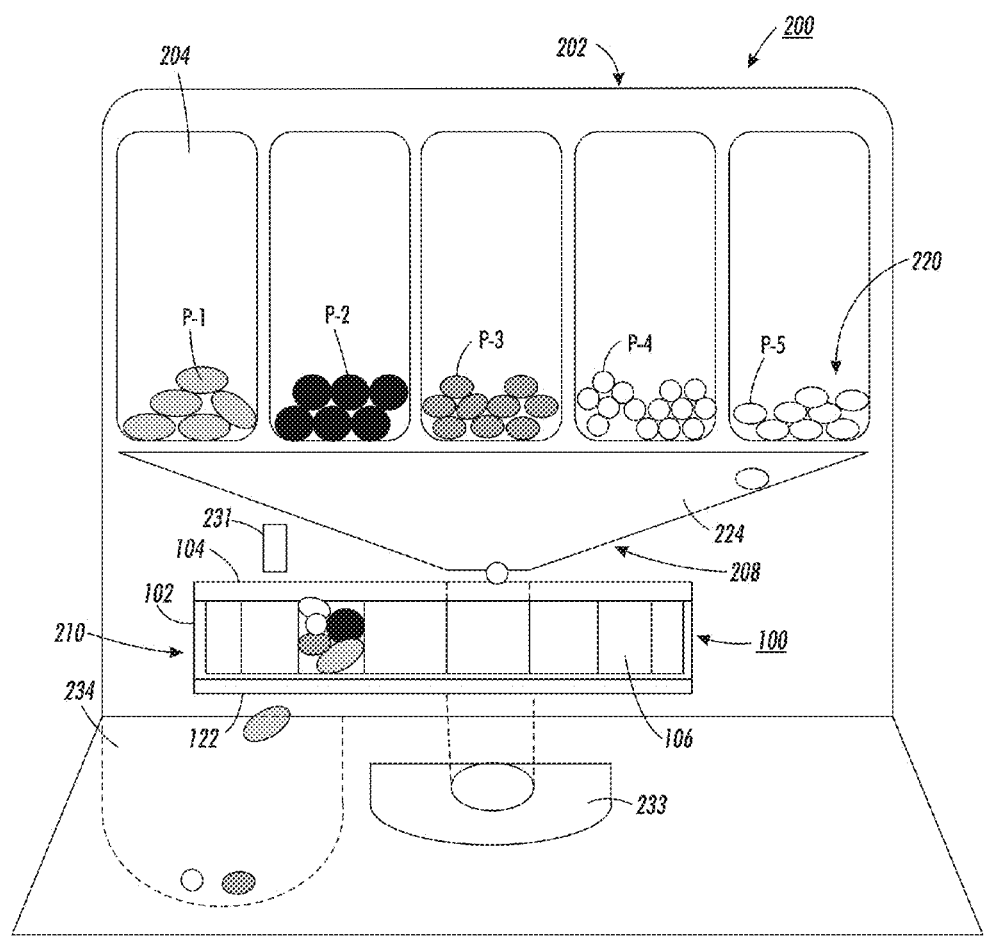
FIG. 10 is a pictorial representation of the apparatus of FIG. 7, emptying unused pills from the portable cassette; and, FIG. 11 is a schematic block diagram of the apparatus in FIG. 7.

FIG. 10 is a pictorial representation of the apparatus of FIG. 7, emptying unused pills from the portable cassette. In an example embodiment, dispenser 202 is configured to empty unused pills P from cassette 100 to prepare cassette 100 for receiving a new combination of pills P. For example, dispenser 202 includes storage compartment 234 and element 210 rotates lid 104 and bottom plate 122 to align with compartment 234. Element 210 then rotates body portion 102 so that each compartment 106 passes over compartment 234 to enable any unused pills to empty into compartment 234.

Figure 11:
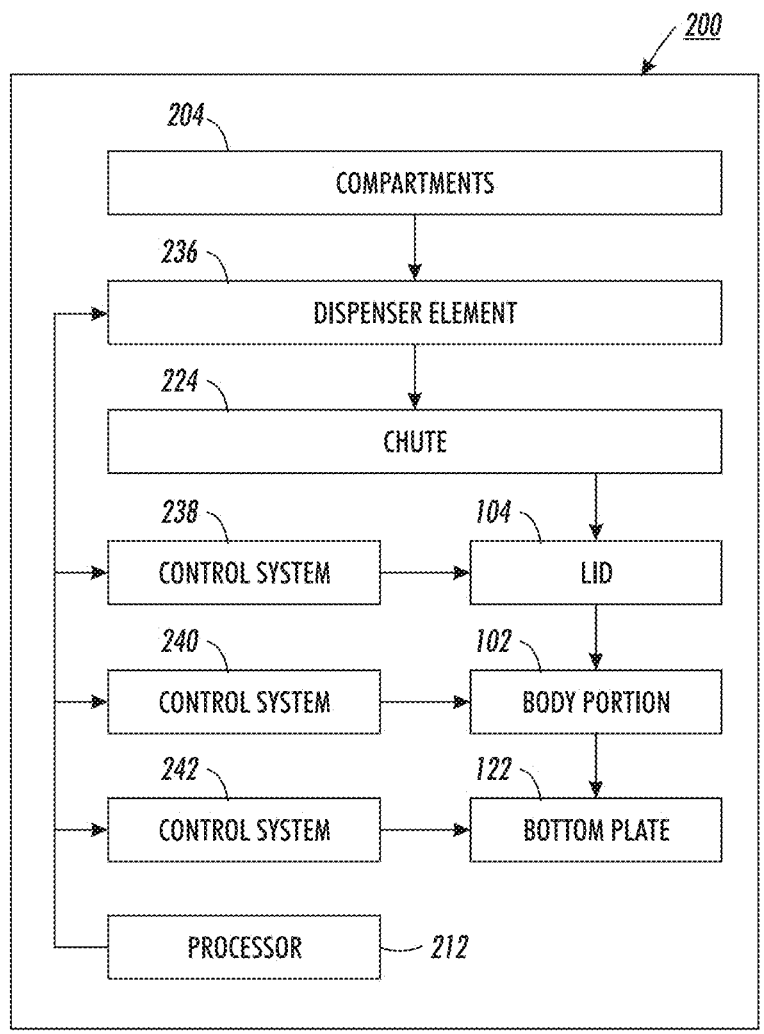

FIG. 11 is a schematic block diagram of apparatus 200. In an example embodiment, dispenser 202 includes dispensing element 236 and control systems 238, 240, and 242. Dispensing element 236 is configured to extract pills P, according to information 216, from compartments 204 and drop the pills into chute 224. The extraction of pills P is coordinated with the positioning of compartments 106. For example, processor 212 associates compartment 106A with a particular day of the week and aligns compartment 106A with chute 224 and element 236. Processor 212 determines the type and number of pills P needed for the particular day of the week and extracts the type and number of pills P needed.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus for dispensing medications, comprising:
   a portable cassette including:
      a body portion including a plurality of cassette compartments; and,
      at least one lid displaceable with respect to the body portion to enable access to the plurality of cassette compartments in a predetermined sequence; and,
   a pill-dispenser including:
      a first processor;
      at least one dispensing compartment arranged to store respective pills of at least one respective medication;
      a dispensing element configured to release the respective pills from the at least one dispensing compartment; and, a cassette element arranged to:
  receive the portable cassette; and,
    displace the portable cassette so that at least one of the respective pills falls into each cassette compartment included in the plurality of cassette compartments, wherein:
after the at least one of the respective pills fall into said each cassette compartment:
  the portable cassette is removable from the pill-dispenser;
  the at least one lid is displaceable to control access to the plurality of cassette compartments;
the first processor is configured to:
  determine when the portable cassette has been removed from and reinserted in the cassette element; and,
  operate, when the portable cassette is determined to be reinserted, the cassette element to identify cassette compartments containing a respective pill.

2. The apparatus of claim 1, wherein:
the first processor configured to receive prescription information including at least one dosage for the at least one medication and at least one schedule for taking the at least one medication; and,
the first processor is configured to control the dispensing element and displace the portable cassette so that the at least one of the respective pills falling into said each cassette compartment is in compliance with the prescription information.

3. The apparatus of claim 1, wherein:
the dispensing element includes a chute arranged to receive the respective pills;
the cassette element is configured to displace the portable cassette to sequentially align the plurality of cassette compartments with the chute so that the at least one of the respective pills falls into said each cassette compartment.

4. The apparatus of claim 3, wherein:
the portable cassette includes a lid with a first opening;
the body portion includes a cylindrical outer wall;
each cassette compartment in the plurality of cassette compartments is formed by a respective pair of side walls extending inward from the outer wall;
the cassette element is configured to:
  rotate the lid so that the first opening is aligned with the chute when the cassette is installed in the pill-dispenser; and,
  rotate the body portion so that said each cassette compartment is aligned with the chute and the first opening so that the at least one of the respective pills falls into said each cassette compartment.

5. The apparatus of claim 4, wherein:
the portable cassette includes a bottom plate with a second opening;
the plurality of compartments includes a pass-through compartment;
the pill-dispenser includes a tray; and,
the cassette element is configured to rotate the lid, the bottom plate, and the body portion so that the first opening, the second opening, and the pass-through compartment, respectively, are aligned with the chute to create a passageway from dispensing compartments to the tray through the portable cassette.

6. The apparatus of claim 5, wherein:
the pill-dispenser includes a storage compartment: and,
when the portable cassette is received in the cassette element, the pill-dispenser is configured to:
  rotate the lid and the bottom plate to align the first and second openings, respectively, with the storage compartment; and,
  rotate the body portion so that some or all of the cassette compartments align with the storage compartment.

7. The apparatus of claim 1, wherein:
the body portion includes a cylindrical outer wall;
each cassette compartment in the plurality of cassette compartments is formed by a respective pair of side walls extending inward from the outer wall;
each cassette compartment has a first shape;
the at least one lid includes a disc with an opening having a second shape substantially matching at least a portion of the first shape; and,
when the portable cassette is removed from the pill-dispenser, the disc is rotatable with respect to the body portion to align the opening with the plurality of compartments.

8. The apparatus of claim 1, wherein:
the portable cassette includes a sensor and a first memory element;
when the portable cassette is removed from the pill-dispenser, the sensor is configured to detect when the at least one lid is displaced to enable access to the plurality of cassette compartments; and,
the first processor is configured to store, in the memory element, respective times for each detection, by the sensor, of displacement of the at least one lid.

9. The apparatus of claim 8, wherein:
the pill-dispenser includes a second processor and a second memory element; and,
the first processor is configured to transmit the respective times to the second processor.

10. The apparatus of claim 9, wherein the second processor is configured to:
receive prescription information including at least one dosage for the at least one medication and at least one schedule for taking the at least one medication;
control the dispensing element and displace the portable cassette so that the at least one of the respective pills falling into said each cassette compartment is in compliance with the prescription information;
transmit the respective time to a computer associated with a health care provider or an entity providing the at least one medication;
receive from the computer, the prescription information modified according to the respective times; and,
control the dispensing element and displace the portable cassette according to the modified prescription information.

11. The apparatus of claim 9, wherein the second processor is configured to:
receive prescription information including at least one dosage for the at least one medication and at least one schedule for taking the at least one medication;
control the dispensing element and displace the portable cassette so that the at least one of the respective pills falling into said each cassette compartment is in compliance with the prescription information; and, transmit the respective time to a computer associated with a health care provider or an entity providing the at least one medication;
store the respective times in the second memory element;
modify the prescription information according to the respective times; and, control the dispensing element and displace the portable cassette according to the modified prescription information.

12. The apparatus of claim 8, wherein the portable cassette includes a wireless transmitter configured to transmit the respective times.

13. The apparatus of claim 1, wherein the first processor is configured to:
receive prescription information including at least one dosage for the at least one medication and at least one schedule for taking the at least one medication;
control the dispensing element and displace the portable cassette so that the at least one of the respective pills falling into said each cassette compartment is in compliance with the prescription information;
transmit the identification of the cassette compartments to a computer associated with a health care provider or an entity providing the at least one medication;
receive from the computer, the prescription information modified according to the identification of the cassette compartments; and,
control the dispensing element and displace the portable cassette according to the modified prescription information.

14. The apparatus of claim 1, wherein the processor is configured to:
receive prescription information including at least one dosage for the at least one medication and at least one schedule for taking the at least one medication;
control the dispensing element and displace the portable cassette so that the at least one of the respective pills falling into said each cassette compartment is in compliance with the prescription information;
store the identification of the cassette compartments containing the respective pill;
modify the prescription information according to the identification of the cassette compartments; and,
control the dispensing element and displace the portable cassette according to the modified prescription information.

15. The apparatus of claim 1, wherein when the portable cassette is removed from the pill-dispenser, the at least one lid is displaceable to:
enable access to the plurality of compartments in a predetermined sequence; and,
block access to the plurality of compartments in a sequence different from the predetermined sequence.

16. A method of dispensing medications, comprising:
receiving, in a pill-dispenser, a portable cassette;
releasing, from at least one dispensing compartment for the pill-dispenser, at least one pill of at least one respective medication stored in the at least one dispensing compartment;
displacing the portable cassette within the pill-dispenser;
receiving at least one of the respective pills into each cassette compartment included in a plurality of cassette compartments of the portable cassette;
after the portable cassette is removed from the pill-dispenser, limiting displacement of at least one lid for the portable cassette to control access to the plurality of cassette compartments; and,
when the cassette is installed in the pill-dispenser:
displacing a lid for the portable cassette to align a first opening in the lid with a chute in the pill-dispenser;
displacing the body portion to align a pass-through compartment included in the plurality of compartments with the chute;
displacing a bottom plate for the cassette to align a second opening in the bottom plate with the chute; and,
creating an open path from the chute to a tray for the pill-dispenser through the first opening, the pass-through compartment, and the second opening.

17. The method of claim 16, further comprising:
receiving, using a processor for the pill-dispenser, prescription information including at least one dosage for the at least one medication and at least one schedule for taking the at least one medication, wherein:
releasing the at least one pill includes releasing the at least one pill according to the prescription information.

18. The method of claim 16, further comprising:
receiving, in a chute for the dispensing element, the respective pills from the at least one dispensing compartment, wherein:
displacing the portable cassette within the pill-dispenser includes displacing the portable cassette to sequentially align the plurality of cassette compartments with the chute.

19. The method of claim 16, wherein:
displacing the portable cassette within the pill-dispenser includes:
displacing, when the cassette is installed in the pill-dispenser, a lid for the portable cassette to align a first opening in the lid with the chute; and,
aligning said each cassette compartment with the chute and the first opening; and,
receiving the at least one of the respective pills into each cassette compartment includes passing the at least one of the respective pills through the first opening.

20. The method of claim 16, further comprising:
when the portable cassette is removed from the pill-dispenser:
detecting, using a sensor for the portable cassette, when the at least one lid is displaced to enable access to the plurality of compartments;
storing, using a first processor for the portable cassette and in a first memory element for the portable cassette, respective times for each detection of displacement of the at least one lid.

21. The method of claim 20, further comprising:
transmitting, using the first processor, the respective times to the second processor.

22. The method of claim 21, further comprising:
receiving, using a second processor for the pill-dispenser, prescription information including at least one dosage for the at least one medication and at least one schedule for taking the at least one medication, wherein:
releasing the at least one pill, displacing the portable cassette, and receiving the at least one of the respective pills includes releasing the at least one pill, displacing the portable cassette, and receiving the at least one of the respective pills in compliance with the prescription information, the method further comprising:
transmitting, using the second processor, the respective time to a computer associated with a health care provider or an entity providing the at least one medication;
receiving, using the second processor, the prescription information modified according to the respective times; and,
releasing the at least one pill, displacing the portable cassette, and receiving the at least one of the respective pills, according to the modified prescription information.

23. The method of claim 21, further comprising:
receiving, using a second processor for the pill-dispenser, prescription information including at least one dosage for the at least one medication and at least one schedule for taking the at least one medication, wherein:
releasing the at least one pill, displacing the portable cassette, and receiving the at least one of the respective pills includes releasing the at least one pill, displacing the portable cassette, and receiving the at least one of the respective pills in compliance with the prescription information, the method further comprising:
storing, using the second processor, the respective times in a second memory element for the pill-dispenser;
modifying, using the second processor, the prescription information according to the respective times; and,
releasing the at least one pill, displacing the portable cassette, and receiving the at least one of the respective pills according to the modified prescription information.

24. The method of claim 20, further comprising:
transmitting, using the first processor, the respective times to a second processor located outside of the portable cassette.

25. The method of claim 24, wherein transmitting the respective times to a second processor includes:
when the portable cassette is located in the pill-dispenser, transmitting the respective time to the second processor located included in the pill-dispenser; or,
using a wireless transmitter included in the portable cassette.

26. The method of claim 16, further comprising:
determining, using a processor for the pill-dispenser, when the portable cassette has been removed from and reinserted in the pill-dispenser; and,
operating, when the portable cassette is determined to be reinserted and using the processor, the cassette element to identify cassette compartments containing a respective pill.

27. The method of claim 26, further comprising:
receiving, using a second processor for the pill-dispenser, prescription information including at least one dosage for the at least one medication and at least one schedule for taking the at least one medication, wherein:
releasing the at least one pill, displacing the portable cassette, and receiving the at least one of the respective pills includes releasing the at least one pill, displacing the portable cassette, and receiving the at least one of the respective pills in compliance with the prescription information, the method further comprising:
transmitting, using the processor, the identification of the cassette compartments to a computer associated with a health care provider or an entity providing the at least one medication;
receiving, using the processor and from the computer, the prescription information modified according to the identification of the cassette compartments; and,
controlling the dispensing element and displacing the portable cassette, using the processor, according to the modified prescription information.

28. The method of claim 26, further comprising:
receiving, using a second processor for the pill-dispenser, prescription information including at least one dosage for the at least one medication and at least one schedule for taking the at least one medication, wherein:
releasing the at least one pill, displacing the portable cassette, and receiving the at least one of the respective pills includes releasing the at least one pill, displacing the portable cassette, and receiving the at least one of the respective pills in compliance with the prescription information, the method further comprising:
storing, using the processor, the identification of the cassette compartments containing the respective pill in a memory element for the pill-dispenser;
modifying, using the processor, the prescription information according to the identification of the cassette compartments; and,
controlling the dispensing element and displacing the portable cassette, using the processor, according to the modified prescription information.

29. The method of claim 16, further comprising, when the portable cassette is removed from the pill-dispenser:
enabling access to the plurality of compartments in a predetermined sequence; and,
blocking access to the plurality of compartments in a sequence different from the predetermined sequence.

30. The method of claim 16, further comprising, when the cassette is installed in the pill-dispenser:
displacing a bottom plate for the cassette to align an opening in the bottom plate with a storage compartment for the pill-dispenser; and,
displacing the body portion to align each cassette compartment in the plurality of cassette compartments, with the opening in the bottom plate and the storage compartment.

31. An apparatus for dispensing medications, comprising:
a portable cassette including:
  a body portion including a plurality of cassette compartments; and,
  at least one lid displaceable with respect to the body portion to enable access to the plurality of cassette compartments in a predetermined sequence; and,
a pill-dispenser including:
  at least one dispensing compartment arranged to store respective pills of at least one respective medication;
  a dispensing element;
  a cassette element arranged to receive the portable cassette;
  a memory element; and,
  a processor configured to:
    receive prescription information including at least one dosage for the at least one medication and at least one schedule for taking the at least one medication;
    operate the dispensing element, according to the prescription information, to release the respective pills from the at least one dispensing compartment;
    operate the cassette element, according to the prescription information, to displace the portable cassette so that at least one of the respective pills falls into each cassette compartment included in the plurality of cassette compartments;
    determine when the portable cassette has been removed from and reinserted in the cassette element;
    operate, when the portable cassette is determined to be reinserted, the cassette element to identify cassette compartments containing a respective pill;
    transmit the identification of the cassette compartments to a computer associated with a health care provider or an entity providing the at least one medication, or store the identification of the cassette compartments in the memory element;

receive from the computer the prescription information modified according to the identification of the cassette compartments, or modify the prescription information according to the identification of the cassette compartments; and, control the dispensing element and displace the portable cassette according to the modified prescription information.

32. A method of dispensing medications, comprising:

receiving, using a processor for a pill-dispenser, prescription information including at least one dosage for at least one medication and at least one schedule for taking the at least one medication;

receiving, in a pill-dispenser, a portable cassette;

releasing, from at least one dispensing compartment for the pill-dispenser, at least one pill of at least one respective medication stored in the at least one dispensing compartment;

displacing the portable cassette within the pill-dispenser;

receiving at least one of the respective pills into each cassette compartment included in a plurality of cassette compartments of the portable cassette;

determining, using the processor, when the portable cassette has been removed from and reinserted in the cassette element;

operating, using the processor, the cassette element to identify cassette compartments containing a respective pill;

transmitting, using the processor, the identification of the cassette compartments to a computer associated with a health care provider or an entity providing the at least one medication, or storing, using the processor, the identification of the cassette compartments in a memory element for the pill-dispenser;

receiving, using the processor and from the computer, the prescription information modified according to the identification of the cassette compartments, or modifying, using the processor, the prescription information; and, releasing the at least one pill, displacing the portable cassette, and receiving the at least one of the respective pills in compliance with the modified prescription information.

* * * * *